(12) United States Patent
Kim et al.

(10) Patent No.: US 8,353,835 B2
(45) Date of Patent: Jan. 15, 2013

(54) ULTRASOUND DIAGNOSTIC SYSTEM AND METHOD FOR DISPLAYING DOPPLER SPECTRUM IMAGES OF MULTIPLE SAMPLE VOLUMES

(75) Inventors: Cheol An Kim, Seoul (KR); Jung Ho Park, Seoul (KR); Seung Woo Park, Seoul (KR); Min Young Park, Seoul (KR); Bong Soo Yoo, Seoul (KR)

(73) Assignees: Medison Co., Ltd., Hongchun-gun (KR); Samsung Life Welfare Foundation, Seoul (KR)

( * ) Notice: Subject to any disclaimer, the term of this patent is extended or adjusted under 35 U.S.C. 154(b) by 136 days.

(21) Appl. No.: 12/840,825

(22) Filed: Jul. 21, 2010

(65) Prior Publication Data

US 2010/0286523 A1    Nov. 11, 2010

Related U.S. Application Data

(62) Division of application No. 11/611,502, filed on Dec. 15, 2006, now Pat. No. 7,798,964.

(30) Foreign Application Priority Data

Dec. 16, 2005 (KR) ............... 10-2005-0124792
Jul. 25, 2006 (KR) ............... 10-2006-0069974
Jul. 31, 2006 (KR) ............... 10-2006-0072111
Aug. 24, 2006 (KR) ............... 10-2006-0080562

(51) Int. Cl.
   *A61B 8/00* (2006.01)

(52) U.S. Cl. .................................... 600/441

(58) Field of Classification Search .......... 600/441
See application file for complete search history.

(56) References Cited

U.S. PATENT DOCUMENTS 5,365,929 A    11/1994    Peterson
(Continued)

FOREIGN PATENT DOCUMENTS

EP    1 016 880 A2    7/2000
(Continued)

OTHER PUBLICATIONS

Piero Tortoli, et al., "Blood Flow Images by a SAW-Based Multigate Doppler System", IEEE Transactions on Ultrasonics, Ferroelectrics, and Frequency Control., vol. 35, No. 5, Sep. 1988, pp. 545-551.

*Primary Examiner* — Tse Chen
*Assistant Examiner* — Saurel J Selkin
(74) *Attorney, Agent, or Firm* — Oblon, Spivak, McClelland, Maier & Neustadt, L.L.P.

(57) ABSTRACT

The embodiment of the present invention provides an ultrasound diagnostic system, including: an ultrasound diagnosis unit for transmitting ultrasound signals to a target object and receiving ultrasound echo signals to acquire B-mode image signals and Doppler spectrum image signals; a processor for forming at least one B-mode image based on the B-mode image signals and forming a plurality of Doppler spectrum images for a plurality of sample volumes designated on the B-mode image based on the Doppler spectrum image signals; a user input unit for allowing a user to input selection information indicating locations and sizes of the plurality of sample volumes; and an image display unit for displaying at least one B-mode image and the plurality of Doppler spectrum images.

8 Claims, 16 Drawing Sheets

U.S. PATENT DOCUMENTS

| | | | |
|---|---|---|---|
| 5,615,680 A | 4/1997 | Sano | |
| 5,622,174 A * | 4/1997 | Yamazaki | 600/441 |
| 6,162,176 A | 12/2000 | Washburn et al. | |
| 6,569,101 B2 | 5/2003 | Quistgaard et al. | |
| 6,592,521 B1 | 7/2003 | Urbano et al. | |
| 2003/0013963 A1 | 1/2003 | Bjaerum et al. | |
| 2003/0199764 A1 | 10/2003 | Kim et al. | |
| 2004/0127798 A1 | 7/2004 | Dala-Krishna et al. | |
| 2007/0287916 A1 | 12/2007 | Kim et al. | |

FOREIGN PATENT DOCUMENTS

| | | |
|---|---|---|
| EP | 1 016 880 A3 | 7/2000 |
| EP | 1 726 262 A1 | 11/2006 |
| JP | 4-75645 | 3/1992 |
| JP | 4-176447 | 6/1992 |
| JP | 6-277218 | 10/1994 |
| JP | 8-84729 | 4/1996 |
| JP | 10-165400 | 6/1998 |
| JP | 11-56848 | 3/1999 |
| JP | 2000-197634 | 7/2000 |
| JP | 2001-46372 | 2/2001 |
| JP | 2001-170051 | 6/2001 |
| JP | 2001-299761 | 10/2001 |
| JP | 2002-606 | 1/2002 |
| JP | 2002-65670 | 3/2002 |
| JP | 2003-52692 | 2/2003 |
| JP | 2003-65675 | 3/2003 |
| JP | 2003-245279 | 9/2003 |
| JP | 2004-739 | 1/2004 |
| WO | WO 01/71376 A1 | 9/2001 |
| WO | WO 03/019227 A1 | 3/2003 |

* cited by examiner

ULTRASOUND DIAGNOSTIC SYSTEM AND METHOD FOR DISPLAYING DOPPLER SPECTRUM IMAGES OF MULTIPLE SAMPLE VOLUMES

The present application is a divisional of U.S. application Ser. No. 11/611,502 filed Dec. 15, 2006, and claims priority from Korean Patent Application Nos. 10-2005-0124792 (filed on Dec. 16, 2005), 10-2006-0069974 (filed on Jul. 25, 2006), 10-2006-0072111 (filed on Jul. 31, 2006) and 10-2006-0080562 (filed on Aug. 24, 2006), the entire subject matters of which are incorporated herein by reference.

BACKGROUND

1. Field

The present invention generally relates to an ultrasound diagnostic system, and more particularly to an ultrasound diagnostic system adapted to provide spectrum images of multiple sample volumes.

2. Background

An ultrasound diagnostic system has become an important and popular diagnostic tool since it has a wide range of applications. Specifically, due to its non-invasive and non-destructive nature, the ultrasound diagnostic system has been extensively used in the medical profession. Modern high-performance ultrasound diagnostic systems and techniques are commonly used to produce two or three-dimensional diagnostic images of internal features of an object (e.g., human organs).

The ultrasound diagnostic system generally uses a wide bandwidth transducer to transmit and receive ultrasound signals. The ultrasound diagnostic system forms images of human internal tissues by electrically exciting an acoustic transducer element or an array of acoustic transducer elements to generate ultrasound signals that travel into the body. The ultrasound signals produce ultrasound echo signals since they are reflected from body tissues, which appear as discontinuities to the propagating ultrasound signals. Various ultrasound echo signals return to the transducer element and are converted into electrical signals, which are amplified and processed to produce ultrasound data for an image of the tissues. The ultrasound diagnostic system is very important in the medical field since it provides physicians with real-time and high-resolution images of human internal features without the need for invasive observation techniques such as surgery.

In the ultrasound diagnostic system, the Doppler effect is used to measure the velocity of red blood cells flowing within a blood vessel or the velocity of heart motion. FIG. 1 shows an example of displaying a B-mode image and a Doppler spectrum at the same time. The B-mode image 11 is an image that displays the brightness, which indicates the intensities of the ultrasound signals reflected from the target object, on a screen. If a user sets a sample volume 13 on a blood vessel 12 in the B-mode image 11 by using a user input interface such as a track ball, then the ultrasound diagnostic system acquires Doppler data of the sample volume and provides a Doppler spectrum image 14 or sound corresponding to the frequency or velocity.

However, since the conventional ultrasound diagnostic system provides Doppler data only for a single sample volume, there is a problem in that the Doppler data corresponding to the sample volumes, which are located elsewhere in the ultrasound image, cannot be provided at the same time.

BRIEF DESCRIPTION OF THE DRAWINGS

Arrangements and embodiments may be described in detail with reference to the following drawings in which like reference numerals refer to like elements and wherein.

DETAILED DESCRIPTION

A detailed description may be provided with reference to the accompanying drawings. One of ordinary skill in the art may realize that the following description is illustrative only and is not in any way limiting. Other embodiments of the present invention may readily suggest themselves to such skilled persons having the benefit of this disclosure.

Figure 1:
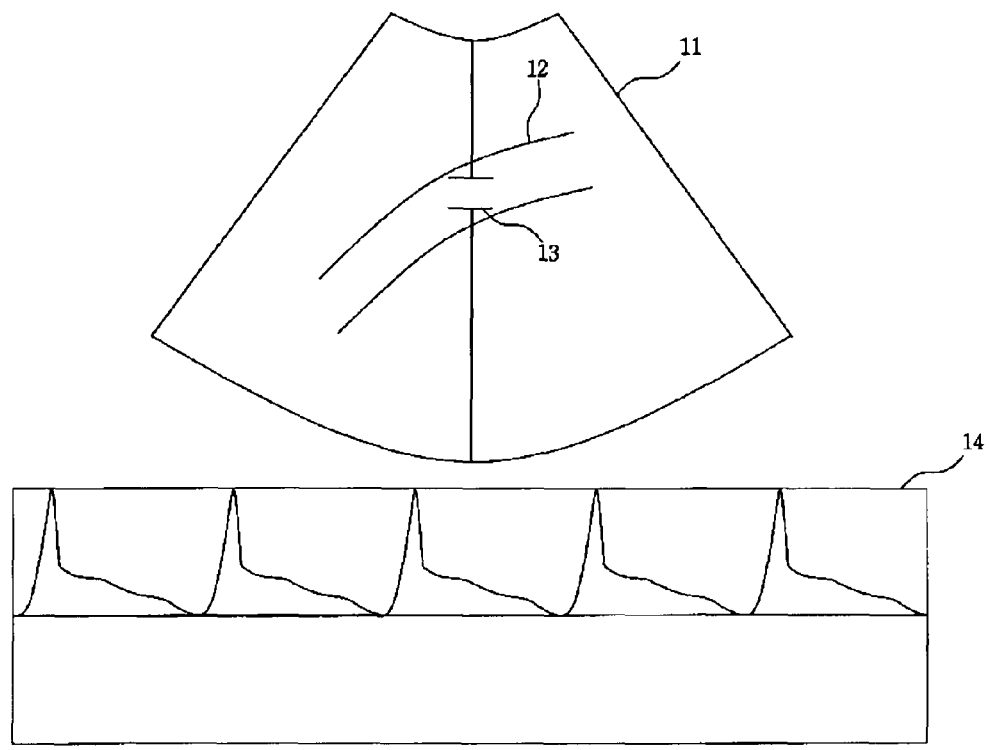
FIG. 1 shows an example of displaying a B-mode image and a Doppler spectrum at the same time in accordance with the prior art.
Figure 2:
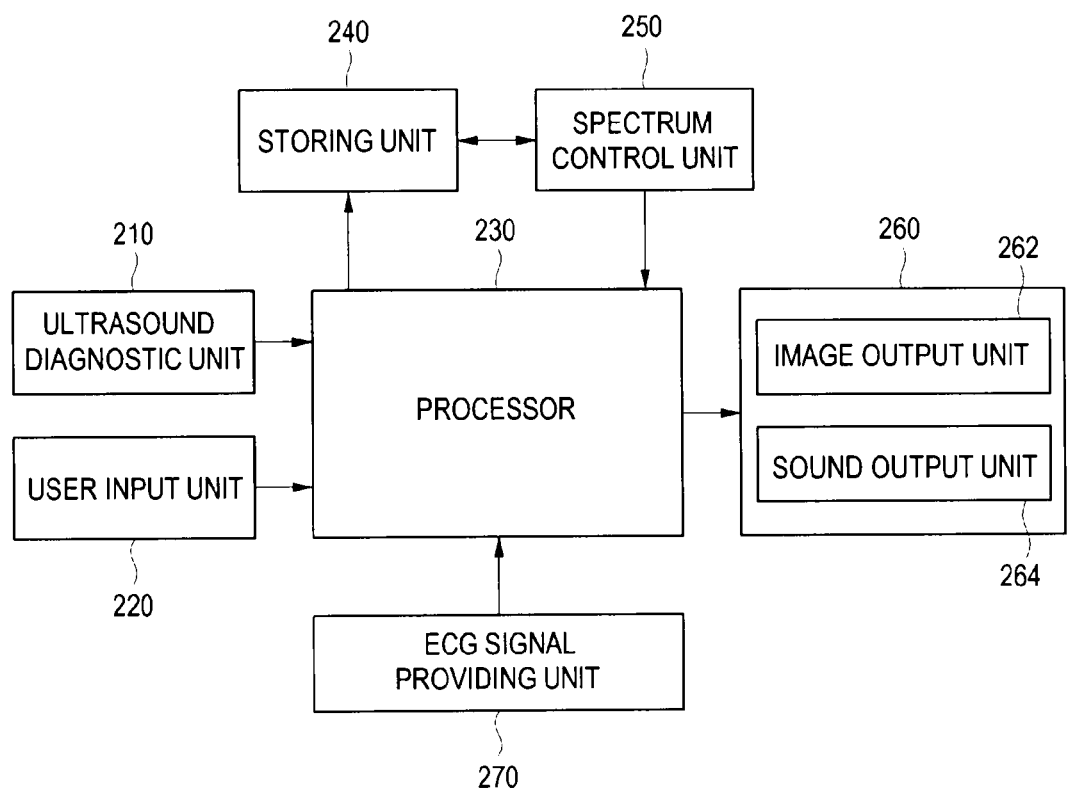
FIG. 2 is a block diagram illustrating an ultrasound diagnostic system constructed in accordance with one embodiment of the present invention.

FIG. 2 is a block diagram illustrating an ultrasound diagnostic system, which is constructed in accordance with one embodiment of the present invention. As shown in FIG. 2, an ultrasound diagnostic system 200 includes an ultrasound diagnosis unit 210, a user input unit 220, a processor 230, a storing unit 240, a spectrum control unit 250 and an output unit 260. The output unit may include an image output unit 262 and a sound output unit 264. The ultrasound diagnostic system 100 may further include an electrocardiogram (ECG) signal providing unit 270.

Figure 3:
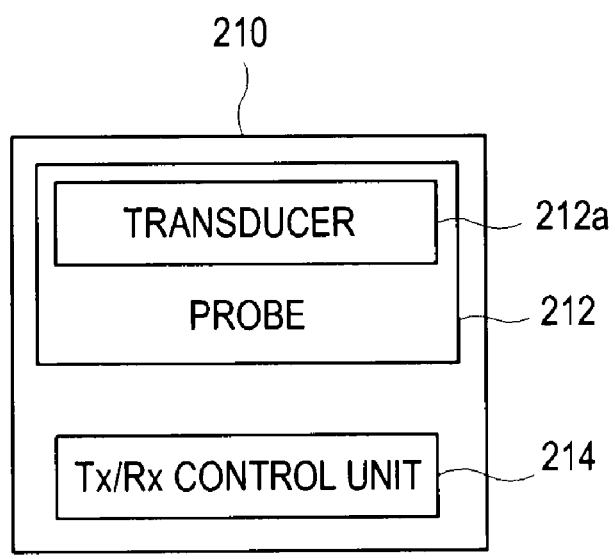
FIG. 3 is a schematic block diagram illustrating an ultrasound diagnosis unit.

The ultrasound diagnosis unit 210 is configured to transmit ultrasound signals to the target object and receive the ultrasound signals reflected from the target object so as to acquire ultrasound scanning information of the target object. Further, the ultrasound diagnosis unit 210 is configured to receive selection information including the locations and sizes of sample volumes designated by the user through the user input unit 220, thereby acquiring Doppler data of the designated sample volumes. The ultrasound diagnosis unit 210 includes: a probe 212 for transmitting the ultrasound signals to the target object and receiving the ultrasound signals reflected from the target object through a plurality of transducers 212a; and a transmission/reception control unit 214 for controlling the transmission/reception of the ultrasound signals as shown in FIG. 3. The probe 212 may be a multi-dimensional array probe including a plurality of transducers. The transmission/reception control unit 214 controls the transmission/reception of the ultrasound signals to obtain ultrasound scanning information for forming the ultrasound images, e.g., the B-mode image of the target object and Doppler data corresponding to a plurality of sample volumes designated on the B-mode image of the target object.

Figure 4:
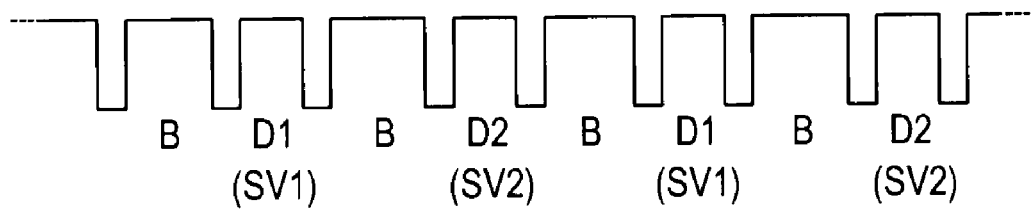
FIG. 4 is a timing diagram illustrating a waveform of a clock used to obtain a B-mode image and Doppler data of sample volumes in accordance with one embodiment of the present invention.

The transmission/reception control unit 214 may alternately transmit/receive ultrasound signals to/from each sample volume so as to obtain the Doppler data. FIG. 4 is a timing diagram illustrating a waveform of a clock used for repeatedly performing a first ultrasound transmission/reception process (B) to obtain a B-mode image and a second ultrasound transmission/reception process (D1, D2) to obtain the Doppler data of the sample volumes. In such a case, the second ultrasound transmission/reception process is alternately carried out for the sample volumes SV1 and SV2.

Figure 5:
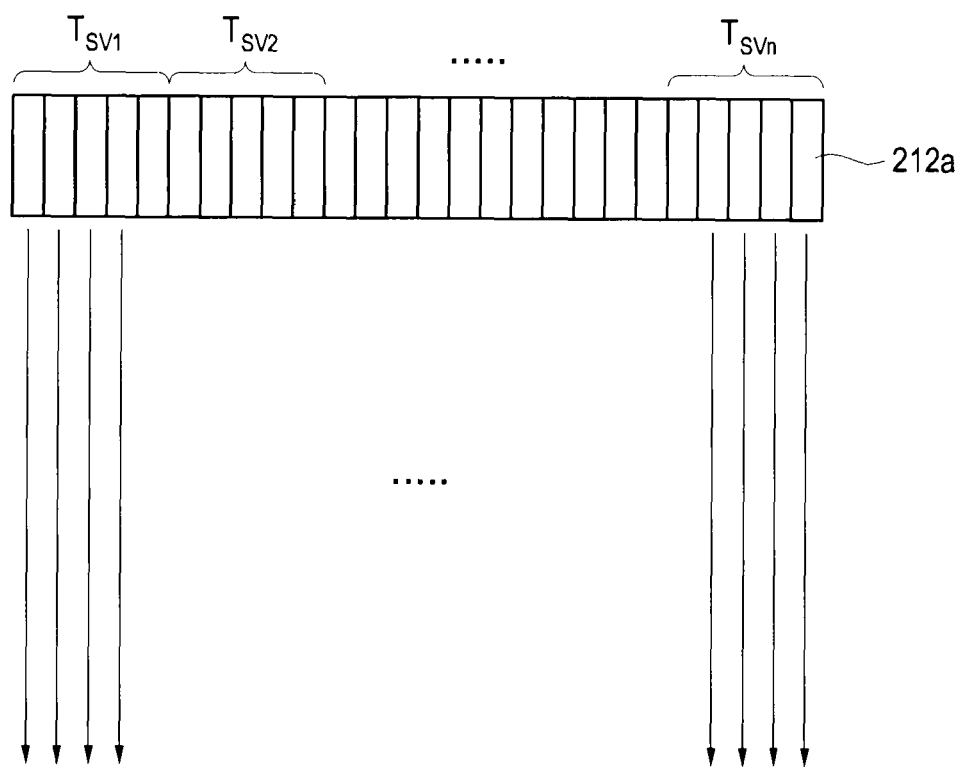
FIG. 5 is a diagram illustrating an example that divides transducers, which are included in a probe, in accordance with the number of sample volumes.
Figure 6:
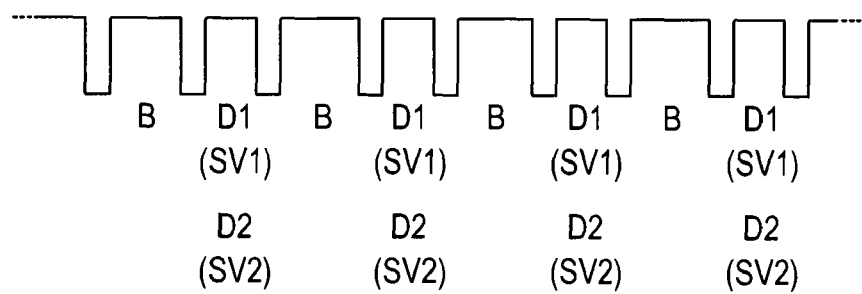
FIG. 6 is a timing diagram illustrating a waveform of a clock used to obtain a B-mode image and Doppler data of sample volumes in accordance with another embodiment of the present invention.

According to another embodiment of the present invention, the transmission/reception control unit 214 is configured to transmit ultrasound signals to a plurality of sample volumes and receive the ultrasound signals reflected from the sample volumes at the same time. The transducers 212a may be divided into several groups in accordance with the number of the sample volumes. As shown in FIG. 5, the transmission/reception control unit 214 controls the transducer groups Tsv1-Tsvn. In such a case, the first ultrasound transmission/reception process (D1) and the second ultrasound transmission/reception process (D2) are alternately executed in synchronization with a clock cycle, as shown in FIG. 6. The ultrasound signals may be simultaneously transmitted to the sample volumes SV1 and SV2 in the second ultrasound transmission/reception process.

Figure 7:
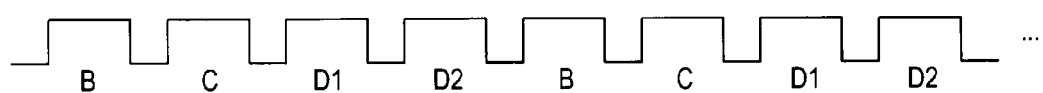
FIG. 7 is a timing diagram illustrating a waveform of a clock used to obtain a B-mode image and Doppler data of sample volumes in accordance with yet another embodiment of the present invention.

In accordance with yet another embodiment of the present invention, the transmission/reception control unit 214 is configured to transmit ultrasound signals to obtain various types of ultrasound images. A B-mode image and a color flow image may be displayed on the screen at the same time. In such a case, the ultrasound transmission/reception processes are alternately executed in synchronization with a clock cycle as shown in FIG. 7. That is, the ultrasound transmission/reception process for obtaining the B-mode image B, the color flow image C and Doppler spectrum images D1 and D2 are alternately and repeatedly carried out. The sample volumes SV1 and SV2 may be set on the color flow image. Also, in such a case, the ultrasound signals may be simultaneously transmitted to the sample volumes SV1 and SV2 for obtaining the Doppler spectrum images D1 and D2.

Figure 8:
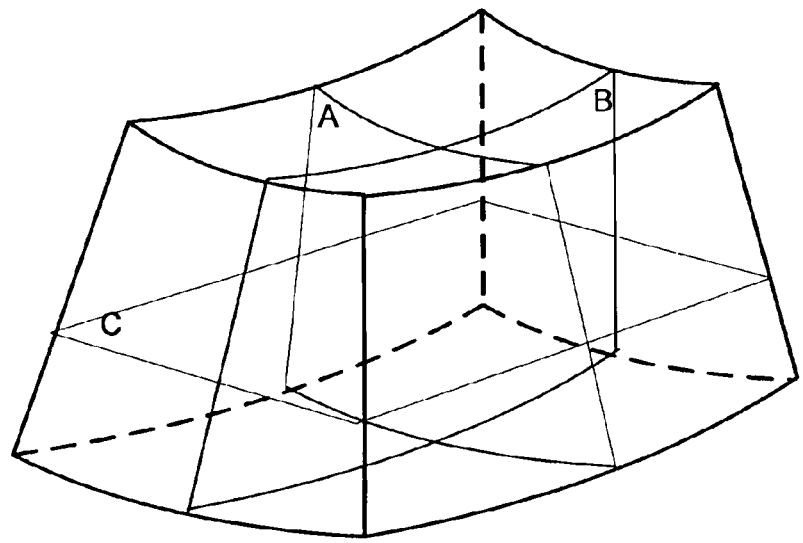
FIG. 8 is a schematic diagram illustrating sectional planes in ultrasound volume data.

The user input unit 220 allows a user to input selection information indicating the locations and sizes of the sample volumes on the B-mode image of the target object. Also, the user input unit 220 receives inputs related to the conditions for displaying a Doppler spectrum of each sample volume such as tissue Doppler spectrum or general Doppler spectrum from the user. The conditions may include baseline, scale, filter value and the like. Further, the input selection information may include color box information for setting a color box, in which the color flow image is displayed, on the B-mode image. Also, the input selection information may include information for selecting sectional planes A, B and C in volume data of the target object for obtaining the B-mode image of the target object as shown in FIG. 8.

Figure 9:
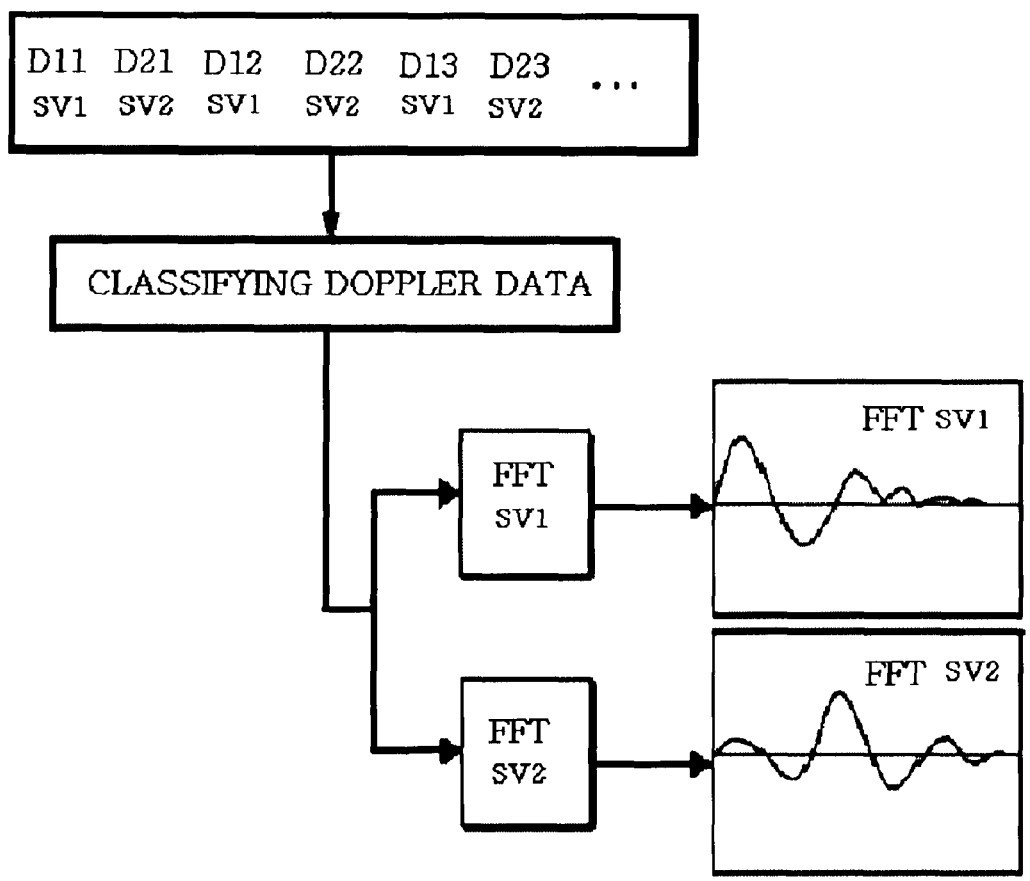
FIG. 9 a schematic diagram illustrating a procedure for producing Doppler spectra of sample volumes.

The processor 230 forms B-mode ultrasound image signals based on the ultrasound scanning information of the target object, which are inputted from the ultrasound diagnosis unit 210. Also, the processor 230 produces Doppler spectrum signals and Doppler sound signals based on the user selection information inputted through the user input unit 220 and the Doppler data. The Doppler spectrum signals include information related to the velocity, frequency or pressure change according to the time change. As shown in FIG. 9, the processor 230 classifies the Doppler data of the plurality of sample volumes, which are inputted from the ultrasound diagnosis unit 210, and applies fast Fourier transformation (FFT) to the classified Doppler data of the sample volumes SV1 and SV2 so as to form the Doppler spectrum signals. The processor 230 may provide the tissue Doppler spectrum or the general Doppler spectrum for the sample volumes at the user's requests, which are inputted through the user input unit 220. The user's request may include base line information and pulse repetition frequency (PRF) information. Then, the processor 230 forms at least one B-mode image based on the B-mode image signals and a plurality of Doppler spectrum images based on the Doppler spectrum signals.

Figure 10:
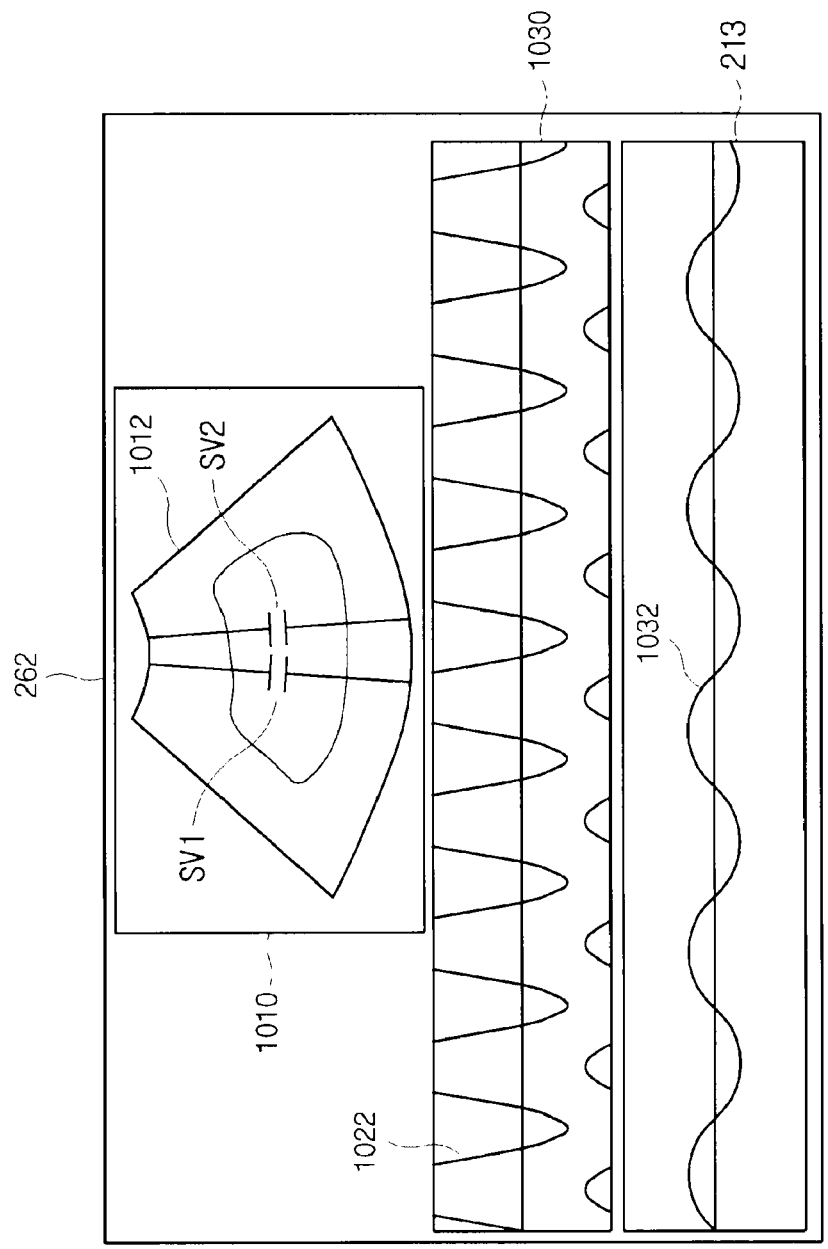
FIG. 10 shows an example of displaying a B-mode image and Doppler spectrum images at the same time in accordance with one embodiment of the present invention.

FIG. 10 shows an example of displaying the B-mode image and Doppler spectrum image at the same time on a screen of the image output unit 262 in accordance with one embodiment of the present invention. As shown in FIG. 10, the B-mode image 1012 is displayed on a first display region 1010. Further, the Doppler spectrum images 1022 and 1032 corresponding to the sample volumes SV1 and SV2, which are classified in the processor 230, are displayed on second and third displayed regions 1020 and 1030 of the image output unit 262, respectively.

Further, the processor 230 may provide Doppler spectrum signals, which are synchronized with an ECG signal inputted from the ECG signal providing unit 270. Also, the processor 230 may provide not only the frequency or velocity change according to the time change, but also the maximum velocity, peak gradient, velocity-time integration, mean velocity, acceleration time, deceleration time, peak systolic velocity (PSV), end diastolic velocity (EDV), resistive index (RI), pulse index (PI), systole/diastole ratio, pressure gradient and heart beating rate.

Figure 11:
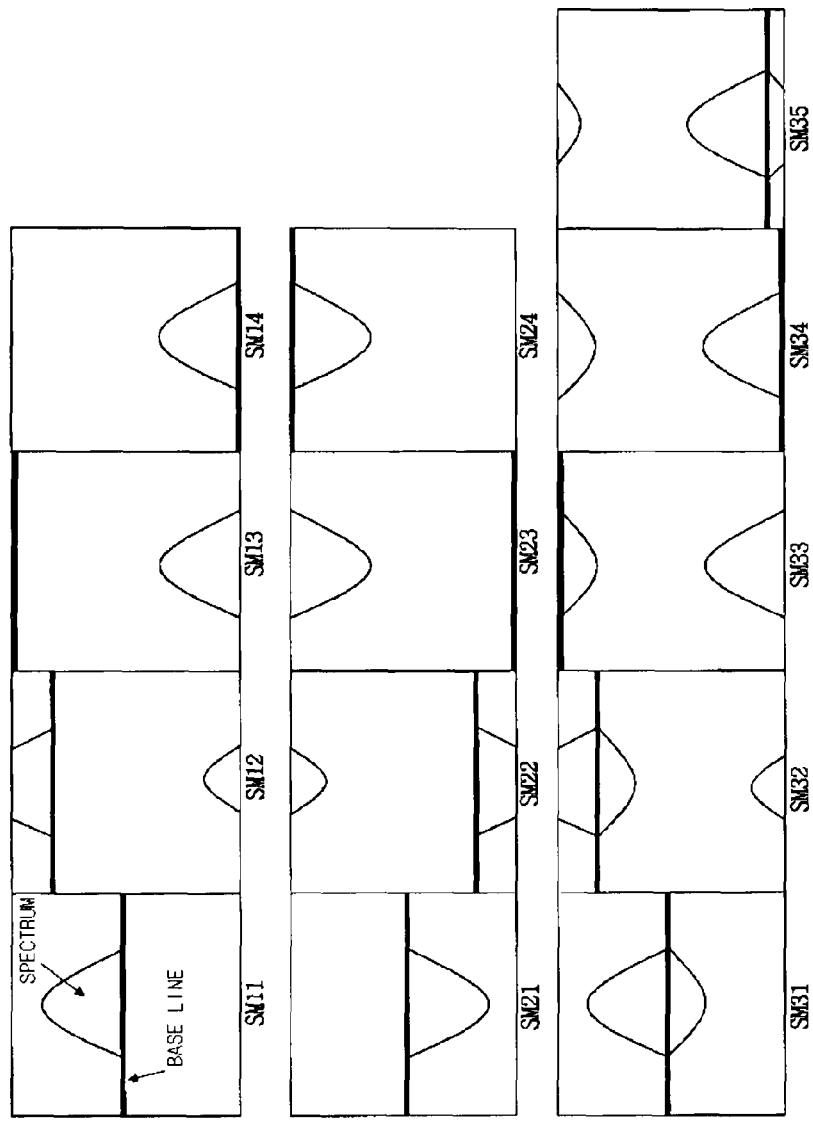
FIG. 11 is a schematic diagram illustrating examples of spectrum models.

The storing unit 240 temporarily stores the B-mode ultrasound image signals and the Doppler spectrum signals received from the processor 230. Further, the storing unit 240 stores a plurality of spectrum models SM11 to SM35 showing the types of Doppler spectra as illustrated in FIG. 11. Also, the storing unit 240 stores an aliasing size of the Doppler spectrum, a spectrum size and information of aliasing levels and spectrum levels. The aliasing size represents the number of aliasing pixels (APs) in the Doppler spectrum image and the spectrum size represents the number of pixels corresponding to a height of Doppler spectrum (hereinafter referred to as the number of spectrum pixels (SPs)), in which the aliasing is not generated, with reference to a base line. The aliasing levels and the spectrum levels are determined based on the numbers of APs and SPs, and may be stored in the storing unit 240 as the following tables.

TABLE 1

| # of AP | 0 | 1-32 | 33-64 | 65-96 | 97-128 | 129-160 | 161-192 | 193-224 | 225-255 |
|---|---|---|---|---|---|---|---|---|---|
| Aliasing level | 0 | 1 | 2 | 3 | 4 | 5 | 6 | 7 | 8 |

TABLE 2

| # of SP | 1-32 | 33-64 | 65-96 | 97-128 | 129-160 | 161-192 | 193-224 | 225-255 |
|---|---|---|---|---|---|---|---|---|
| Spectrum level | 7 | 6 | 5 | 4 | 3 | 2 | 1 | 0 |

The spectrum control unit 250 acquires Doppler spectrum images of each sample volume based on the Doppler spectrum signals stored in the storing unit 240. The spectrum control unit 250 analyzes the Doppler spectrum images based on the plurality of spectrum models SM11 to SM35 stored in the storing unit 240, thereby determining spectrum models corresponding to the Doppler spectrum images.

In order to determine the spectrum models corresponding to the Doppler spectrum images of each sample volume, the spectrum control unit 250 detects an intensity of each pixel consisting of the Doppler spectrum images and compares the detected intensity of each pixel with a first threshold. If the pixel intensity is greater than the first threshold, then the spectrum control unit 250 determines the corresponding pixel as a contour pixel of the Doppler spectrum image. After detecting the contour of the Doppler spectrum image, the spectrum control unit 250 determines the spectrum models corresponding to the Doppler spectrum images based on the detected contours.

Figure 12:
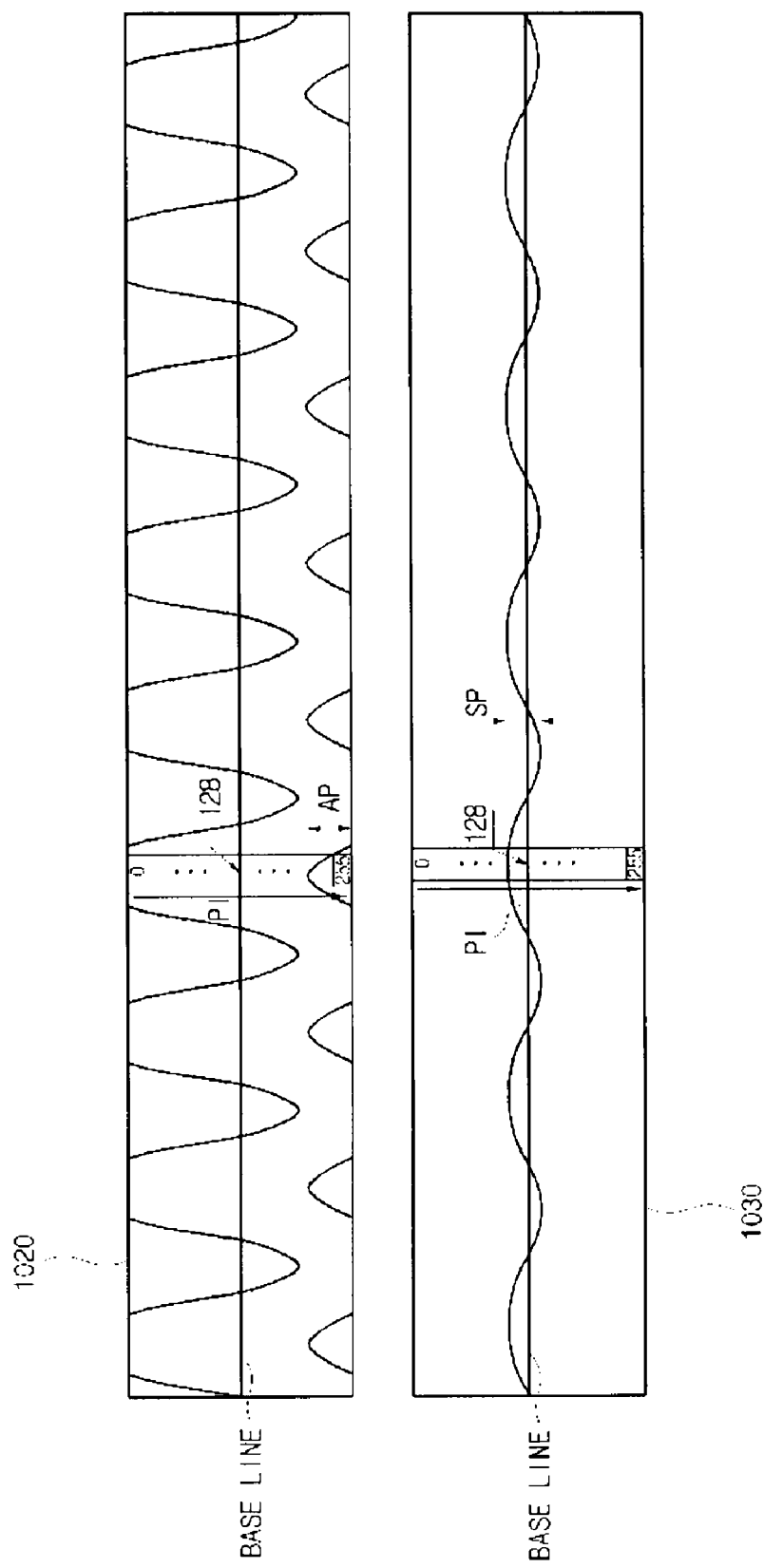
FIG. 12 is a schematic diagram illustrating an example of showing pixel indices, aliasing size and spectrum size.

Subsequently, the spectrum control unit 250 sets pixel indices (PI) on the pixels existing in the same column of each Doppler spectrum image. For example, the spectrum control unit 250 sets PI on the Doppler spectrum images corresponding to sample volumes SV1 and SV2, respectively, as shown in FIG. 12. The spectrum control unit 250 analyzes pixels of the Doppler spectrum images corresponding to PIs to check whether the aliasing is generated. If it is determined that the aliasing is generated, then the spectrum control unit 250 calculates the number of APs at each column of the Doppler spectrum image, in which the aliasing is generated, and then detects a maximum number of APs of each Doppler spectrum image. The spectrum control unit 250 detects PIs corresponding to the base lines of each Doppler spectrum image, in which the aliasing is generated.

The spectrum control unit 152 checks whether the aliasing can be removed by adjusting the base line based on the PI of the base line and the maximum PI. If it is determined that the aliasing can be removed by adjusting the base line, then the spectrum control unit 152 adjusts the base line of the corresponding Doppler spectrum image by referencing the detected PI of the base line and the maximum PI.

Figure 13:
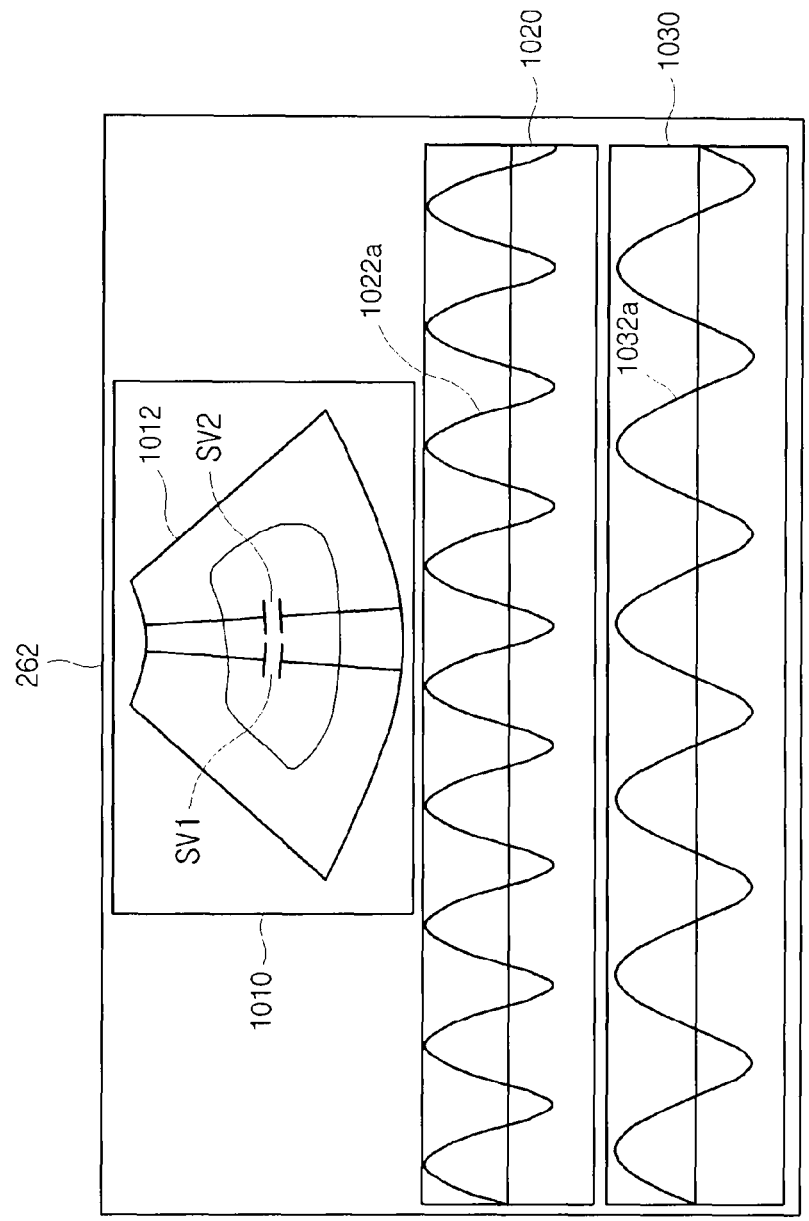
FIG. 13 shows an example of simultaneously displaying a B-mode image and Doppler spectrum images with base lines and pulse repetition frequencies adjusted in accordance with one embodiment of the present invention.

On the other hand, if it is determined that the aliasing cannot be removed by adjusting the base line, then the spectrum control unit 250 determines an aliasing level corresponding to the maximum number of APs of the Doppler spectrum image by referencing information (Table 1) stored in the storing unit 240. The spectrum control unit 250 adjusts PRF for the corresponding sampling volume based on the detected aliasing level. The spectrum control unit 250 sets the increment of PRF differently according to the aliasing level. The spectrum control unit increases PRF based on an increment of PRF determined by the aliasing level, thereby obtaining a Doppler spectrum image 1022a with the aliasing removed from the Doppler spectrum image 1022 as shown in FIG. 13.

Further, if it is determined that the aliasing is not generated in the Doppler spectrum image, then the spectrum control unit 250 calculates the number of SPs of each column in the Doppler spectrum images, in which the aliasing is not generated, based on PI and then detects a maximum SP of each Doppler spectrum image. The spectrum control unit 250 determines a spectrum level corresponding to the maximum SP by referencing information (Table 2) stored in the storing unit 240. The spectrum control unit 250 checks whether the spectrum level is less than a second threshold for adjusting PRF. If it is determined that the spectrum level is greater than the second threshold, then the PRF is not adjusted. On the other hand, if it is determined that the spectrum level is less than the second threshold, then the spectrum control unit 250 adjusts PRF for the sample volume of the Doppler spectrum image in which the aliasing is not generated. For example, if the spectrum level is less than 3, then the spectrum control unit 250 may decrease PRF, thereby obtaining a Doppler spectrum image 1032a adjusting PRF of the Doppler spectrum image 1032 as shown in FIG. 13.

Figure 14:
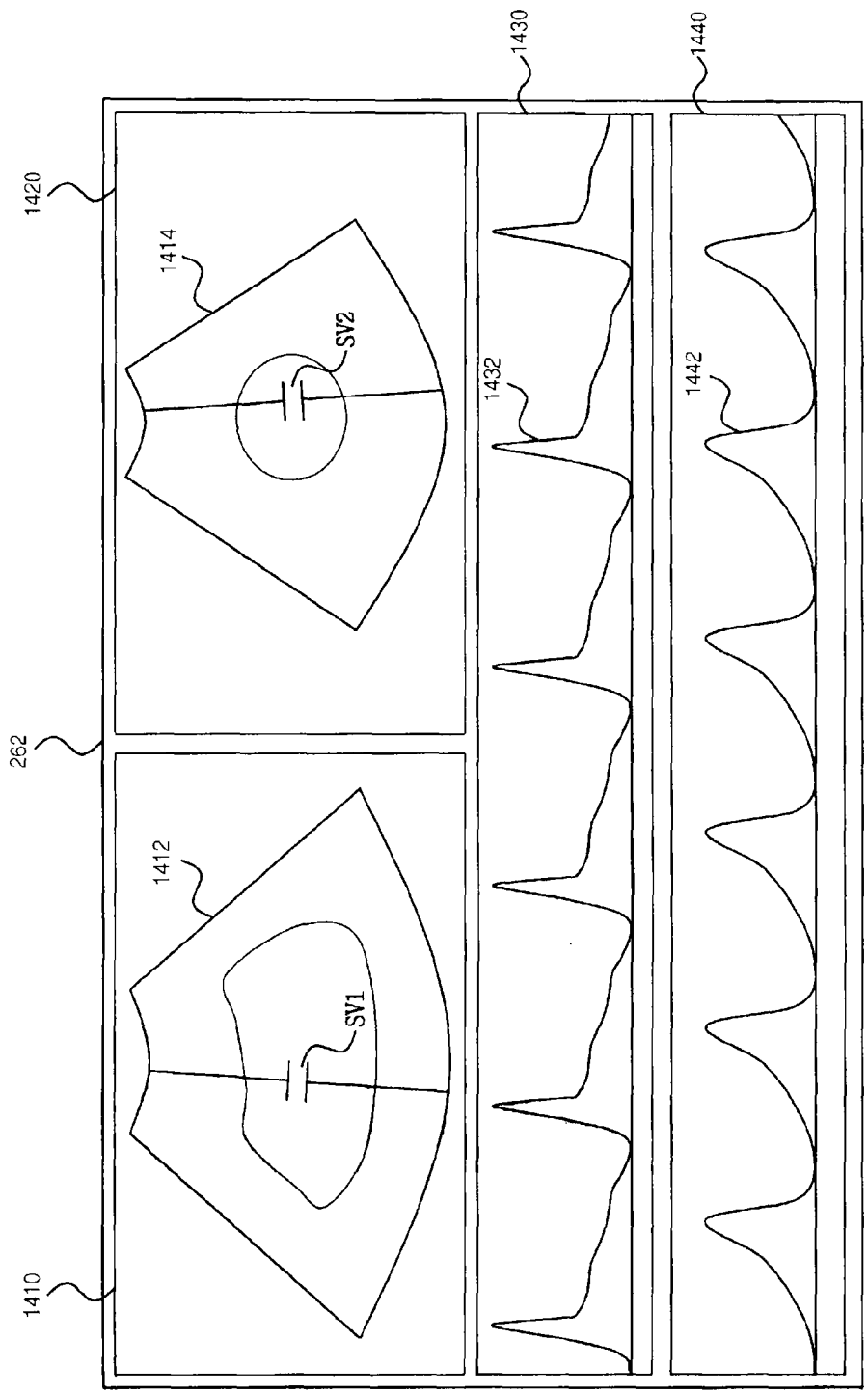
FIG. 14 shows an example of displaying two B-mode images and Doppler spectrum images in accordance with another embodiment of the present invention.

The output unit 260 includes an image output unit 262 and a sound output unit 264. The image output unit 262 displays the B-mode image, Doppler spectrum and ECG waveform by receiving the B-mode image signals, Doppler spectrum signals and ECG signals from the processor 230. The image output unit 262 may display a plurality of the B-mode images, wherein each B-mode image is obtained from different sectional planes in the ultrasound volume data of the target object based on the input selection information inputted in the user input unit 220 as shown in FIG. 14. As shown in FIG. 14, a first B-mode image 1110 and a second B-mode image 1120, which are obtained from different section planes, e.g., A and B sectional planes shown in FIG. 8, are displayed on first and second display regions 1410 and 1420 of the image output unit 262, respectively. The first sample volume SV1 may be set on the first B-mode image 1412 and the second sample volume SV2 may be set on the second B-mode image 1414.

Figure 15:
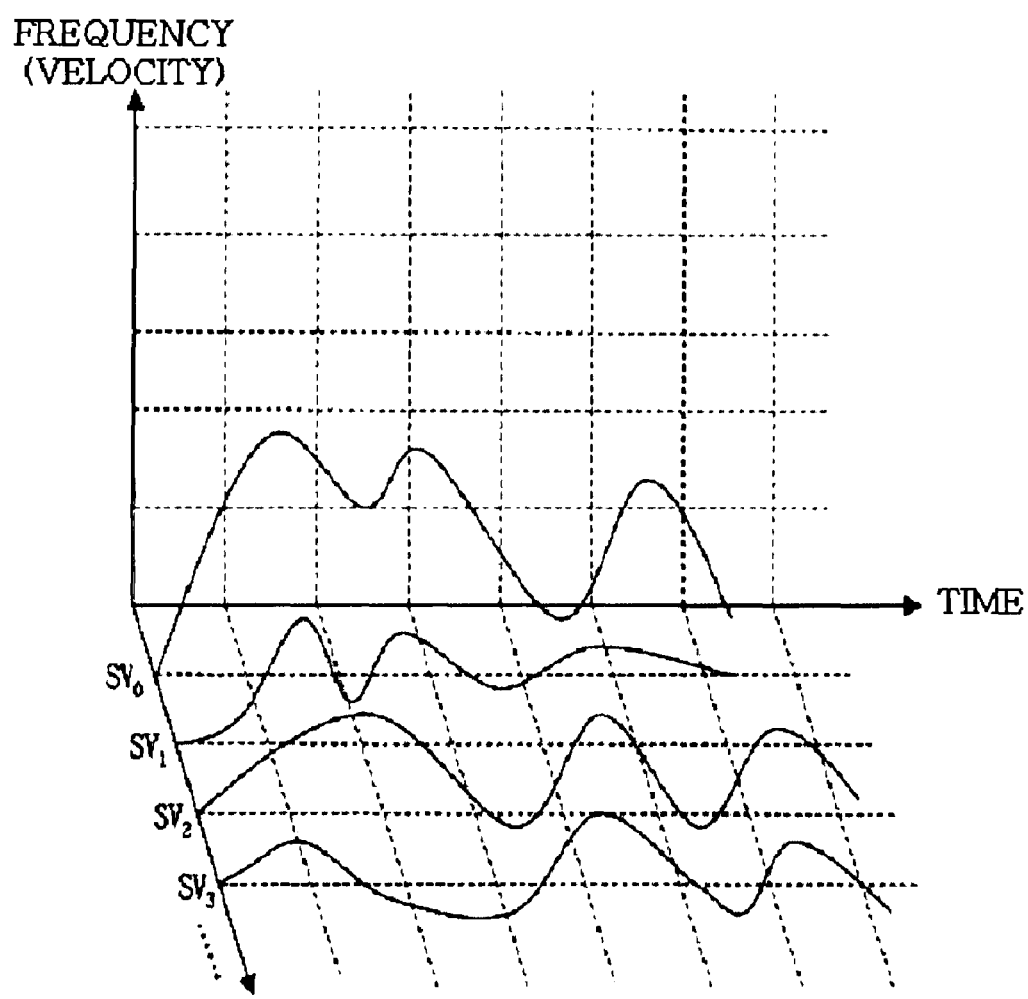
FIGS. 15 and 16 are diagrams illustrating examples of displaying a plurality of Doppler spectrum images in accordance with the present invention.
Figure 16:
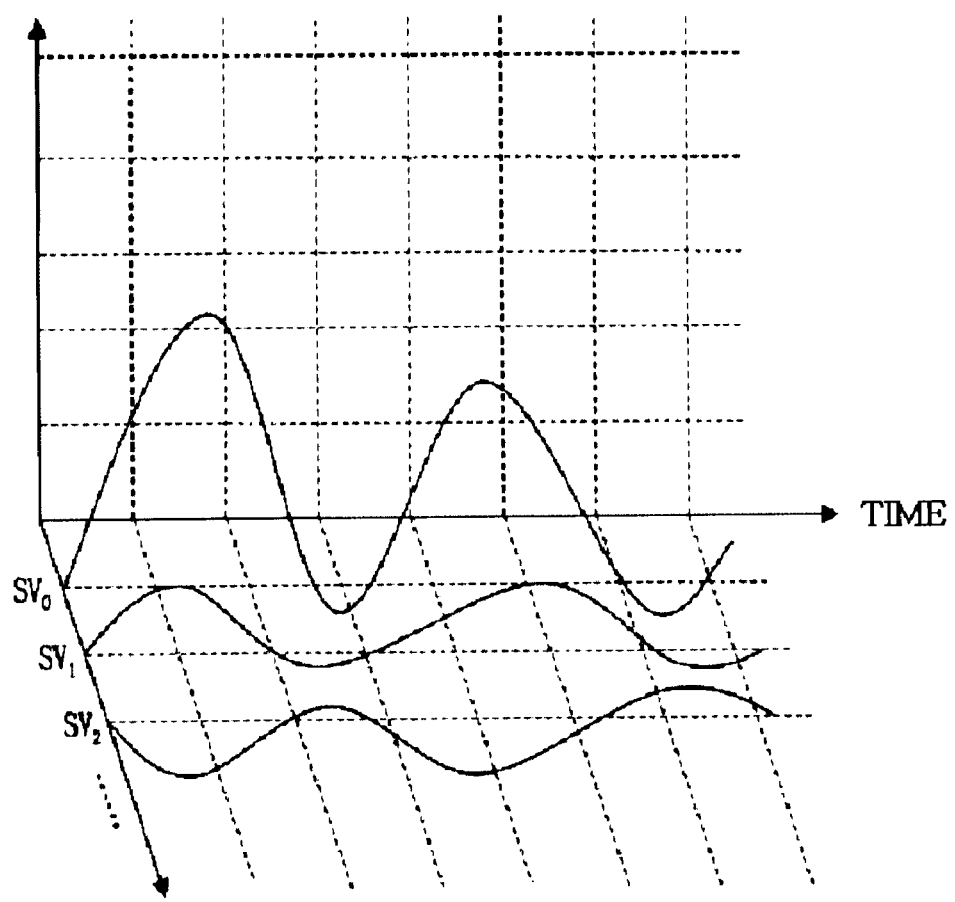

Also, various types of Doppler spectrum image may be displayed. For example, spectrum images corresponding to a plurality of sample volumes SV0, SV1, SV2 . . . may be displayed on the image display unit 262 at the same time, as shown in FIGS. 15 and 16. The Doppler spectrum images shown in FIG. 15 represent the frequency (or velocity) changes of the sample volumes with time (t), while the Doppler spectrum images shown in FIG. 12 represent the pressure changes of the sample volumes with time (t). The Doppler spectrum images shown in FIGS. 15 and 16 may be displayed together with the B-mode image.

Figure 17:
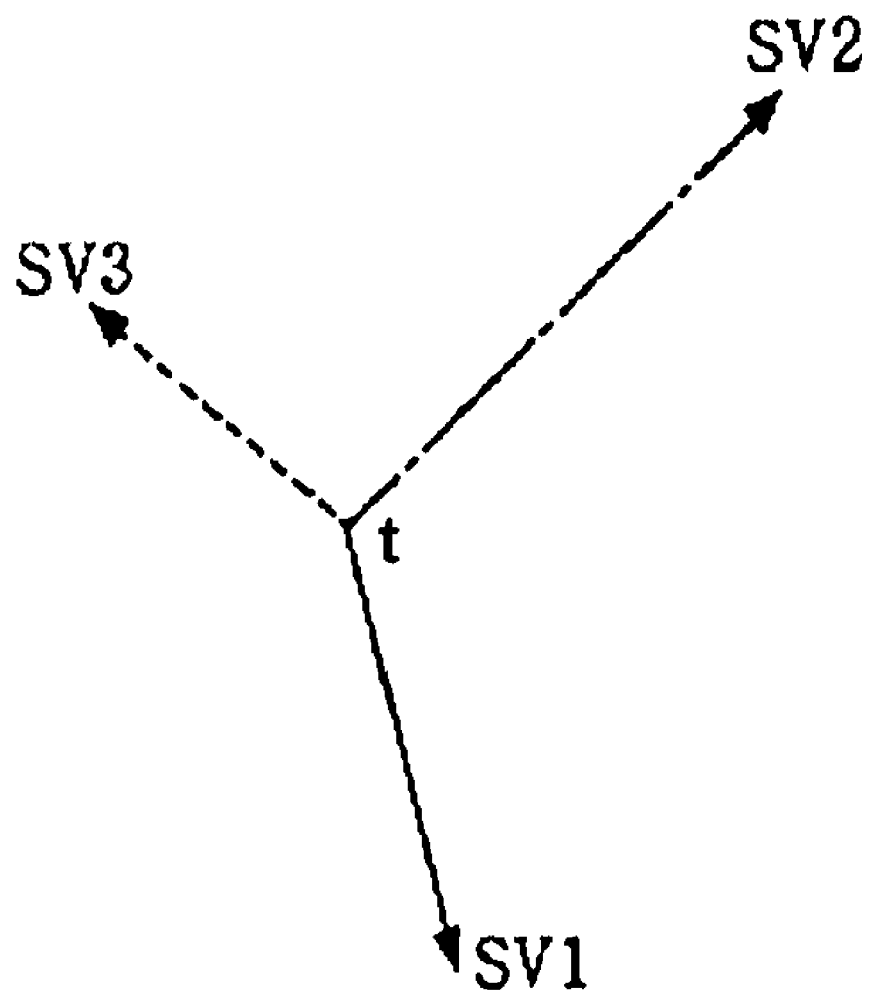
FIG. 17 is a diagram illustrating Doppler spectra of sample volumes, which correspond to axes of a 3-dimensional graph.
Figure 18:
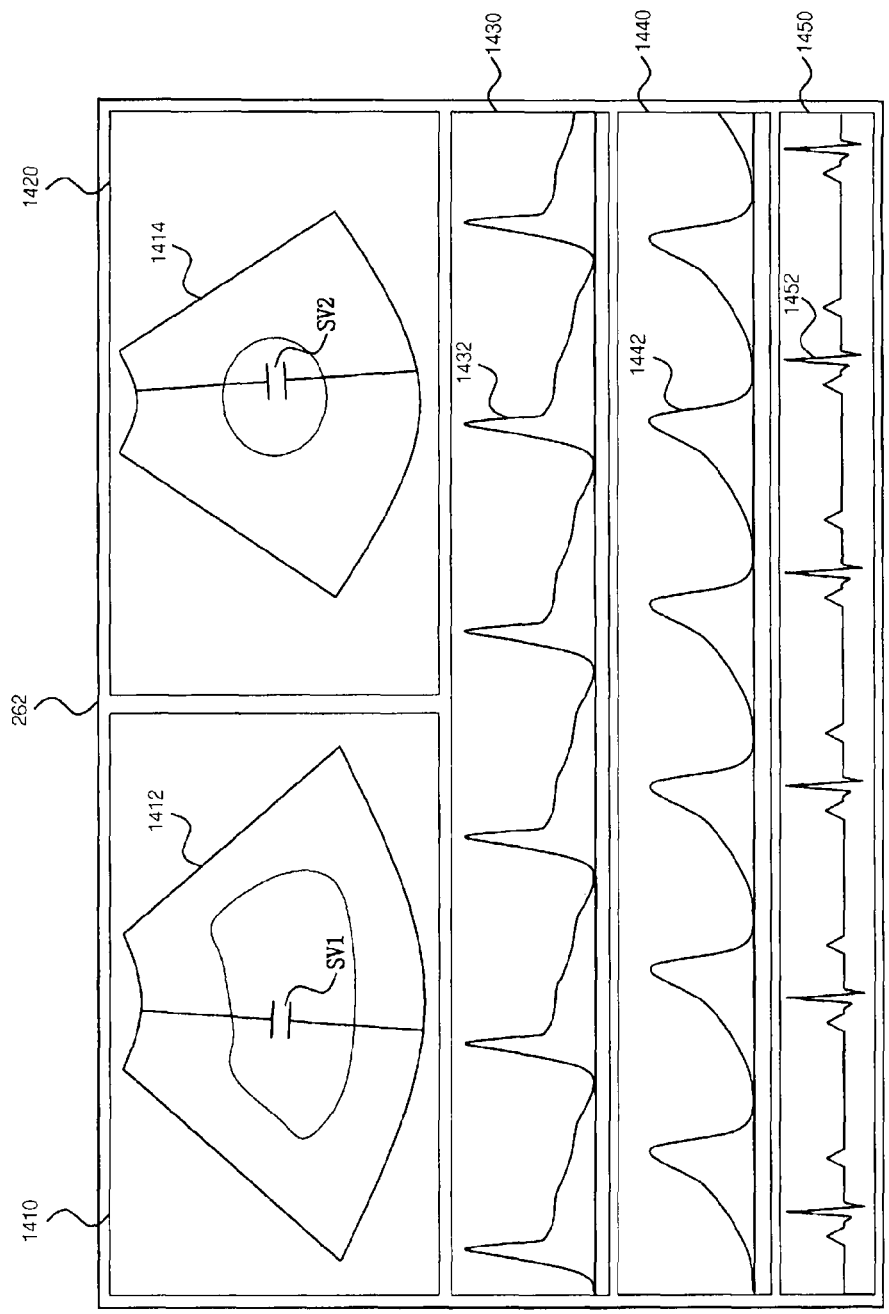
FIG. 18 shows an example of displaying two B-mode images and Doppler spectrum images synchronized with ECG signals in accordance with yet another embodiment of the present invention.

FIG. 17 is a diagram showing Doppler spectra of the sample volumes, which correspond to each axis of a 3-dimensional graph. FIG. 18 is a diagram showing an example displaying Doppler spectrum images 1432 and 1442 of two sample volumes SV1 and SV2 designated by the user together with an ECG waveform 1452 displayed on a fifth display region 1450 of the image output unit 262. The Doppler spectrum images 1432 and 1442 show the frequency (or velocity) changes with time.

Figure 19:
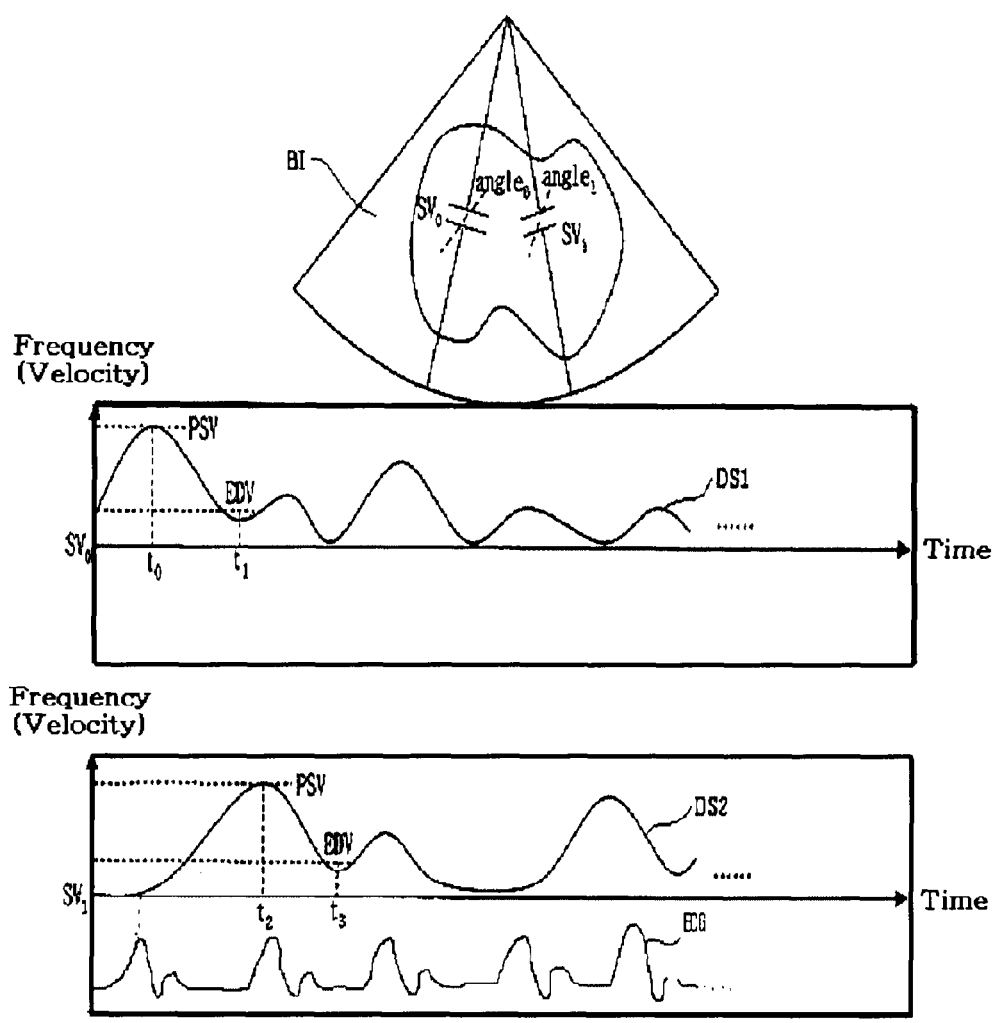
FIG. 19 shows an example of displaying a B-mode image, Doppler spectrum images synchronized with ECG signals in accordance with still another embodiment of the present invention.

Further, in accordance with one embodiment of the present invention, as to displaying a plurality of Doppler spectrum images together with the ECG waveform, the time difference between PSV and EDV detected from the Doppler spectra of the sample volumes can be easily recognized in real time as shown in FIG. 19.

Further, an example directed to simultaneously displaying the Doppler spectra of the sample volumes on a single screen is disclosed in accordance with one embodiment of the present invention. Also, the Doppler spectra of the sample volumes may be separately displayed on different screens.

The sound output unit 264 includes a plurality of speakers. The sounds of the sample volumes may be time divided and sequentially outputted. Alternatively, the sounds of the sample volumes may be outputted through different speakers. Also, the sound components detected from the sample volumes may be synthesized with a predetermined weight or synthesis coefficient by using the following equation:

$$SND = a \times SND_{SV1} + (1-a) \times SND_{SV2} \qquad (1)$$

Wherein, SND represents a final sound output, a represents a synthesis coefficient, and $SND_{SV1}$ and $SND_{SV2}$ represent sound components corresponding to the sample volumes.

In accordance with the present invention, the ultrasound diagnostic system can individually adjust the sizes, baselines, scales and filter values of at least two different sample volumes. Also, the spectrum change representing the frequency change or velocity change within a specific period of the ECG signal can be provided with numerical values. Furthermore, the peak and mean traces can be measured on the Doppler spectra of the sample volumes. Further, the time difference of a specific event between the two sample volumes can be measured.

As mentioned above, the Doppler spectra and the sounds of the sample volumes designated at different places on the ultrasound image can be provided at the same time. Further, the base line and the PRF of the Doppler spectrum images corresponding to the sample volumes set on the B-mode image are automatically adjusted in accordance with one embodiment of the present invention. Thus, the aliasing can be easily removed from the Doppler spectrum image.

In accordance with one embodiment of the present invention, there is provided an ultrasound diagnostic system, including: an ultrasound diagnosis unit for transmitting ultrasound signals to a target object and receiving ultrasound echo signals to acquire B-mode image signals and Doppler spectrum image signals; a processor for forming at least one B-mode image based on the B-mode image signals and forming a plurality of Doppler spectrum images for a plurality of sample volumes designated on the B-mode image based on the Doppler spectrum image signals; a user input unit for allowing a user to input selection information indicating locations and sizes of the plurality of sample volumes; and an image display unit for displaying at least one B-mode image and the plurality of Doppler spectrum images.

In accordance with another embodiment of the present invention, there is provided a method of forming ultrasound images, including: a) forming at least one B-mode image of a target object; b) setting a plurality of sample volumes on the B-mode image; c) forming Doppler spectrum images corresponding to each of the plurality of sample volumes; and d) displaying the B-mode images together with the Doppler spectrum images.

Any reference in this specification to "one embodiment," "an embodiment," "example embodiment," etc. means that a particular feature, structure or characteristic described in connection with the embodiment is included in at least one embodiment of the invention. The appearances of such phrases in various places in the specification are not necessarily all referring to the same embodiment. Further, when a particular feature, structure or characteristic is described in connection with any embodiment, it is submitted that it is within the purview of one skilled in the art to effect such feature, structure or characteristic in connection with other ones of the embodiments.

Although embodiments have been described with reference to a number of illustrative embodiments thereof, it should be understood that numerous other modifications and embodiments can be devised by those skilled in the art that will fall within the spirit and scope of the principles of this disclosure. More particularly, numerous variations and modifications are possible in the component parts and/or arrangements of the subject combination arrangement within the scope of the disclosure, the drawings and the appended claims. In addition to variations and modifications in the component parts and/or arrangements, alternative uses will also be apparent to those skilled in the art.

What is claimed is:

1. A method of displaying ultrasound images, comprising:
a) forming at least one B-mode image of a target object;
b) displaying said at least one B-mode image on a screen of a display unit;
c) allowing a user to input selection information indicating location and sizes of a plurality of sample volumes on the displayed at least one B-mode through a user input unit;
d) forming a plurality of Doppler spectrum images corresponding to each of the plurality of sample volumes, wherein the forming d) includes:
d1) providing spectrum models indicating types of Doppler spectrum images, and aliasing levels determined by a number of aliasing pixels and spectrum levels determined by a number of spectrum pixels in the Doppler spectrum images;
d2) detecting contours of each Doppler spectrum image;
d3) determining spectrum models corresponding to each Doppler spectrum image based on the detected contours;
d4) setting a plurality of pixel indices on each Doppler spectrum image in a vertical direction of the base lines; and
d5) adjusting the base lines and the pulse repetition frequencies of the Doppler spectrum images based on the determined spectrum models and the pixel indices; and
e) displaying the B-mode images together with the Doppler spectrum images at the same time.

2. The method of claim 1, wherein the adjusting d5) includes:
d51) checking whether aliasing is generated in each Doppler spectrum images based on the determined spectrum models and the pixel indices;
d52) if the aliasing is generated, detecting an aliasing size of the Doppler spectrum images based on the pixel indices;
d53) detecting a pixel index corresponding to the base line of the Doppler spectrum images;
d54) checking whether the aliasing is removed by adjusting the base lines;

d55) if it is determined that the aliasing is removed, adjusting the base lines of the corresponding sample volumes; and d56) adjusting the pulse repetition frequencies based on the detected aliasing size.

3. The method of claim 2, wherein the adjusting d56) includes:

determining an aliasing level corresponding to the detected aliasing size by referencing the provided plurality of aliasing levels; and adjusting the pulse repetition frequencies based on the determined aliasing level.

4. The method of claim 2, wherein the adjusting d5) includes:

d57) if the aliasing is not generated, detecting a spectrum size of the Doppler spectrum images; and d58) adjusting the pulse repetition frequencies of corresponding sample volumes based on detected spectrum size.

5. The method of claim 4, wherein the adjusting d58) includes:

comparing the detected spectrum size with a threshold to determine whether to adjust the pulse repetition frequencies;

if the spectrum size is less than the threshold in the comparison result, determining a spectrum level corresponding to the detected spectrum size by referencing the provided spectrum levels; and adjusting the pulse repetition frequencies based on the determined spectrum level.

6. The method of claim 1, further comprising providing an ECG signal, wherein the Doppler spectrum signals of the selected sample volumes are in synchronization with the ECG signal.

7. The method of claim 1, further comprising forming a color flow image.

8. The method of claim 7, wherein the B-mode image, the Doppler spectrum image and the color flow image are alternately and repeatedly formed.

* * * * *